United States Patent
Zhang et al.

(10) Patent No.: US 11,198,686 B2
(45) Date of Patent: *Dec. 14, 2021

(54) CRYSTAL FORM AND SALT FORM OF PYRIDONE COMPOUND AND PREPARATION METHOD THEREFOR

(71) Applicants: GUANGZHOU JOYO PHARMATECH CO., LTD., Guangdong (CN); SHIJIAZHUANG SAGACITY NEW DRUG DEVELOPMENT CO, LTD., Hebei (CN); MEDSHINE DISCOVERY INC., Jiangsu (CN)

(72) Inventors: Lei Zhang, Shanghai (CN); Bin Chen, Shanghai (CN); Yangguang Zhao, Shanghai (CN); Jian Li, Shanghai (CN); Shuhui Chen, Shanghai (CN)

(73) Assignees: GUANGZHOU JOYO PHARMATECH CO., LTD., Guangdong (CN); SHLIAZHUANG SAGACITY NEW DRUG DEVELOPMENT CO., LTD., Hebei (CN); MEDSHINE DISCOVERY INC., Jiangsu (CN)

( * ) Notice: Subject to any disclaimer, the term of this patent is extended or adjusted under 35 U.S.C. 154(b) by 0 days.

This patent is subject to a terminal disclaimer.

(21) Appl. No.: 16/755,386

(22) PCT Filed: Oct. 12, 2018

(86) PCT No.: PCT/CN2018/110022
§ 371 (c)(1),
(2) Date: Apr. 10, 2020

(87) PCT Pub. No.: WO2019/072236
PCT Pub. Date: Apr. 18, 2019

(65) Prior Publication Data
US 2021/0206753 A1   Jul. 8, 2021

(30) Foreign Application Priority Data
Oct. 13, 2017 (CN) .......................... 201710953047.3

(51) Int. Cl.
*C07D 409/14* (2006.01)
*A61P 11/00* (2006.01)
*A61K 31/4436* (2006.01)

(52) U.S. Cl.
CPC ............ *C07D 409/14* (2013.01); *A61P 11/00* (2018.01); *C07B 2200/13* (2013.01)

(58) Field of Classification Search
CPC ... C07D 409/14; A61P 11/00; C07B 2200/13; A61K 31/4436
See application file for complete search history.

(56) References Cited

U.S. PATENT DOCUMENTS

2019/0062315 A1* 2/2019 Shih ........................ A61P 11/00

FOREIGN PATENT DOCUMENTS

| CN | 102099036 A | 6/2011 |
|----|-------------|--------|
| CN | 104822687 A | 8/2015 |
| CN | 106459042 A | 2/2017 |
| EP | 3444247 A1 | 2/2019 |
| WO | 2009149188 A1 | 12/2009 |
| WO | 2014055548 A1 | 4/2014 |
| WO | 2015153683 A1 | 10/2015 |
| WO | 2017177974 A1 | 10/2017 |

OTHER PUBLICATIONS

Margaritopoulos, G.A., "Pirfenidone in the treatment of idiopathic pulmonary fibrosis: an evidence-based review of its place in therapy." Core Evidence 11 (2016): 11-22.*
Jan. 17, 2019 International Search Report issued in International Patent Application No. PCT/CN2018/110022.
Jan. 17, 2019 Written Opinion of the International Searching Authority issued in International Patent Application No. PCT/CN2018/110022.
Chinese Patent Application No. 201710953047.3 (not published).

* cited by examiner

*Primary Examiner* — John M Mauro
(74) *Attorney, Agent, or Firm* — Harness, Dickey & Pierce, P.L.C.

(57) ABSTRACT

A crystal form of a compound 1 and a method for preparing the same, further comprising an application of the crystal form in the preparation of a drug for treating diseases associated with fibrosis.

19 Claims, 2 Drawing Sheets

Compound 1

CRYSTAL FORM AND SALT FORM OF PYRIDONE COMPOUND AND PREPARATION METHOD THEREFOR

CROSS-REFERENCE TO RELATED APPLICATIONS

This application is a 371 National Phase of International Application No. PCT/CN2018/110022, filed Oct. 12, 2018, which claims the benefit of Chinese Patent Application No. CN 201710953047.3, filed Oct. 13, 2017. The entire disclosure of the above application is incorporated herein by reference.

FIELD OF THE INVENTION

The present disclosure relates to a crystal form of Compound 1 and a preparation method thereof, and also relates to a use of the crystal form in manufacturing a medicament for treating fibrosis-related diseases.

BACKGROUND OF THE INVENTION

Idiopathic Pulmonary Fibrosis (IPF) is a typical chronic, progressive and fatal fibrotic interstitial pneumonia characterized by progressive dyspnea and a gradual decline in lung function, which quickly lead to respiratory failure and death. In 2008, it was estimated that at least 5 million people worldwide suffered from IPF, but the patients rose to 130,000 to 500,000 people only in the United States in 2010. About 48,000 new cases were reported and about 40,000 people died of IPF each year. The incidence of IPF is estimated to be 4.6-7.4/100,000, and 30,000 to 35,000 new cases are diagnosed each year. The incidence among smokers is much higher than that of non-smokers and can reach nearly 2.3% in people with a smoking history of 20-40 years. The incidence among males is higher than that of females. The 5-year individual survival rate of IPF patients is about 20%, and the mortality rate is much higher than that of many cancers, thus it is known as a cancer-like disease without cancer name actually. Potential risk factors include occupational exposure and environmental pollution such as metals, animals, wood chips, smoking and smog.

The pathogenesis of IPF is complex and is generally thought to involve interactions between pro-inflammatory and pro-fibrotic pathways, but the exact mechanism is still unknown. In 2014, both Roche's Pirfenidone and Boehringer Ingelheim's Nintedanib were first approved by FDA in the US, and the annual sales of Pirfenidone is estimated to reach 2 billion dollars total in 2019. Not only the prognosis of IPF is poor at present, but also the therapeutical methods are scarce. The approval of these two new drugs gives confidence in the clinical treatments of IPF disease, and these drugs are likely to be used for treating other fibrotic diseases. However, there are still unsatisfied clinical demands for large quantity of patients, thus the development of novel better IPF drugs has attracted increasing attentions.

CONTENT OF THE INVENTION

The present disclosure provides a crystal form A of Compound 1, wherein the X-ray powder diffraction pattern thereof comprises characteristic peaks at diffraction angle 2θ of 7.87±0.2°, 15.69±0.2° and 16.58±0.2°.

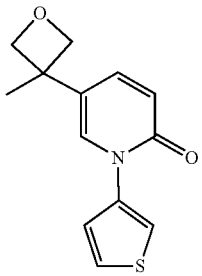

Compound 1

In some embodiments of the present disclosure, the X-ray powder diffraction pattern of the crystal form A of Compound 1 as mentioned above comprises characteristic peaks at diffraction angle 2θ of 7.87±0.2°, 15.69±0.2°, 16.58±0.2°, 18.34±0.2°, 19.39±0.2°, 24.97±0.2°, 27.19±0.2° and 31.57±0.2°.

In some embodiments of the present disclosure, the XRPD pattern of the crystal form A of Compound 1 as mentioned above is as shown in FIG. 1.

In some embodiments of the present disclosure, the analytical data of the XRPD pattern of the crystal form A of Compound 1 as mentioned above are as shown in Table 1.

TABLE 1

Analytical data of the XRPD pattern of the crystal form A

| No. | 2θ Angle (°) | Interplanar spacing (Å) | Relative intensity (%) |
|---|---|---|---|
| 1 | 7.874 | 11.2185 | 100.0 |
| 2 | 15.692 | 5.6426 | 58.6 |
| 3 | 16.580 | 5.3423 | 40.8 |
| 4 | 18.339 | 4.8338 | 34.2 |
| 5 | 18.697 | 4.7420 | 11.1 |
| 6 | 19.109 | 4.6407 | 26.4 |
| 7 | 19.388 | 4.5745 | 35.2 |
| 8 | 19.942 | 4.4486 | 7.3 |
| 9 | 20.293 | 4.3725 | 19.8 |
| 10 | 20.568 | 4.3146 | 23.4 |
| 11 | 21.814 | 4.0710 | 19.4 |
| 12 | 22.111 | 4.0169 | 19.7 |
| 13 | 22.524 | 3.9442 | 12.2 |
| 14 | 24.973 | 3.5627 | 39.7 |
| 15 | 25.430 | 3.4996 | 24.2 |
| 16 | 26.180 | 3.4010 | 49.0 |
| 17 | 27.187 | 3.2773 | 29.5 |
| 18 | 27.659 | 3.2225 | 4.6 |
| 19 | 29.575 | 3.0180 | 8.2 |
| 20 | 30.981 | 2.8841 | 4.1 |
| 21 | 31.571 | 2.8315 | 39.9 |
| 22 | 31.888 | 2.8041 | 8.0 |
| 23 | 33.483 | 2.6740 | 7.9 |
| 24 | 34.868 | 2.5710 | 5.1 |
| 25 | 39.726 | 2.5710 | 21.6 |

In some embodiments of the present disclosure, the differential scanning calorimetry curve of the crystal form A of Compound 1 as mentioned above has an endothermic peak with an onset at 106.63° C.±4° C.

In some embodiments of the present disclosure, the DSC pattern of the crystal form A of Compound 1 as mentioned above is as shown in FIG. 2.

In some embodiments of the present disclosure, the thermogravimetric analysis curve of the crystal form A of Compound 1 as mentioned above has a weight loss of 0.3391% occurred at 110.00° C.±3° C.

In some embodiments of the present disclosure, the TGA pattern of the crystal form A of Compound 1 as mentioned above is as shown in FIG. 3.

The present disclosure also provides a method for preparing the crystal form A of Compound 1, comprising adding the Compound 1 existing in any form to an organic mixed solvent of an ester solvent and an alkane solvent and slurrying to obtain the crystal form A of Compound 1.

In some embodiments of the present disclosure, the ester solvent is ethyl acetate.

In some embodiments of the present disclosure, the alkane solvent is selected from petroleum ether, n-heptane and cyclohexane.

In some embodiments of the present disclosure, the organic mixed solvent is a mixed solvent of ethyl acetate and n-heptane.

In some embodiments of the present disclosure, the volume ratio of the ethyl acetate to n-heptane is 1:0.5-1.5.

In some embodiments of the present disclosure, the volume ratio of the ethyl acetate to n-heptane is 1:1.

In some embodiments of the present disclosure, the slurrying is performed at a temperature of 20° C. to 30° C.

In some embodiments of the present disclosure, the duration of the slurrying is 12 hours to 36 hours.

In some embodiments of the present disclosure, the weight ratio of the Compound 1 to the organic mixed solvent is 1:5-6.

The present disclosure also provides a use of the crystal form A in the manufacture of a medicament for treating idiopathic pulmonary fibrosis.

Technical Effect

The crystal form A of Compound 1 of the present disclosure has good stability and is suitable for the manufacture of medicaments. It has a significant inhibitory effect on cytokines associated with the TNF-α/TGF-β pathway, and it also exhibits a significant inhibitory effect on idiopathic pulmonary fibrosis indicated by SD rat left unilateral pulmonary fibrosis model.

Definitions and Explanations

Unless otherwise indicated, the following terms and phrases used herein are intended to have the following meanings. A particular term or phrase should not be considered uncertain or unclear without a special definition, but should be understood according to its ordinary meaning. When a trade name appears herein, it is intended to refer to its corresponding product or its active ingredient.

The intermediate compounds of the present disclosure can be prepared by a variety of synthetic methods known to those skilled in the art, including the specific embodiments described below, the combination of the embodiments described below with other chemical synthesis methods and equivalent alternatives known in the art. The preferred embodiments include, but are not limited to, the embodiments of the present disclosure.

The chemical reactions of the specific embodiments of the present disclosure are performed in suitable solvents, and the solvents should be suitable for the chemical change of the present disclosure and the reagents and materials required for the same. In order to obtain the compounds of the present disclosure, it is sometimes necessary for those skilled in the art to modify or select the synthetic steps or reaction schemes based on the existing embodiments.

The present disclosure will be described in detail below through embodiments, which do not imply any limitation to the present invention.

All solvents used in the present disclosure are commercially available and can be directly used without further purification.

The present disclosure adopts following abbreviations: DMF refers to N,N-dimethylformamide; MsOH refers to methanesulfonic acid; EtOH refers to ethanol; MeOH refers to methanol; NaOH refers to sodium hydroxide; DCM refers to dichloromethane; PE refers to petroleum ether; EtOAc refers to ethyl acetate; THF refers to tetrahydrofuran.

Compounds are named either manually or by using ChemDraw®, or using vendors catalogue name if commercially available.

X-Ray Powder Diffractometer (XRPD) of the Present Disclosure

Instrument model: Bruker D8 advance X-ray diffractometer

Detection method: about 10-20 mg of the sample was used for XRPD detection.

The detailed XRPD parameters were as follows:

X-ray tube: Cu, Kα, (λ=1.54056Å)

X-ray tube voltage: 40 kV, X-ray tube current: 40 mA

Divergence slit: 0.60 mm

Detector slit: 10.50 mm

Anti-scattering slit: 7.10 mm

Scanning range: 4-40 deg

Step size: 0.02 deg

Step time: 0.12 seconds

Rotation speed of sample tray: 15 rpm

Differential Scanning Calorimeter (DSC) of the Present Disclosure

Instrument model: TA Q2000 differential scanning calorimeter

Detection method: samples (about 1 mg) were placed in a DSC aluminum crucible for detection, and heated from 25° C. to 350° C. with a heating rate of 10° C./min under the condition of 50 mL/min $N_2$.

Thermal Gravimetric Analyzer (TGA) of the Present Disclosure

Instrument model: TA Q5000 thermal gravimetric analyzer

Detection method: samples (2 mg to 5 mg) were placed in a TGA platinum crucible for detection, and heated from room temperature to a weight loss of 20% with a heating rate of 10° C./min under the condition of 25 mL/min $N_2$.

DETAILED DESCRIPTION OF THE PREFERRED EMBODIMENT

Figure 1:
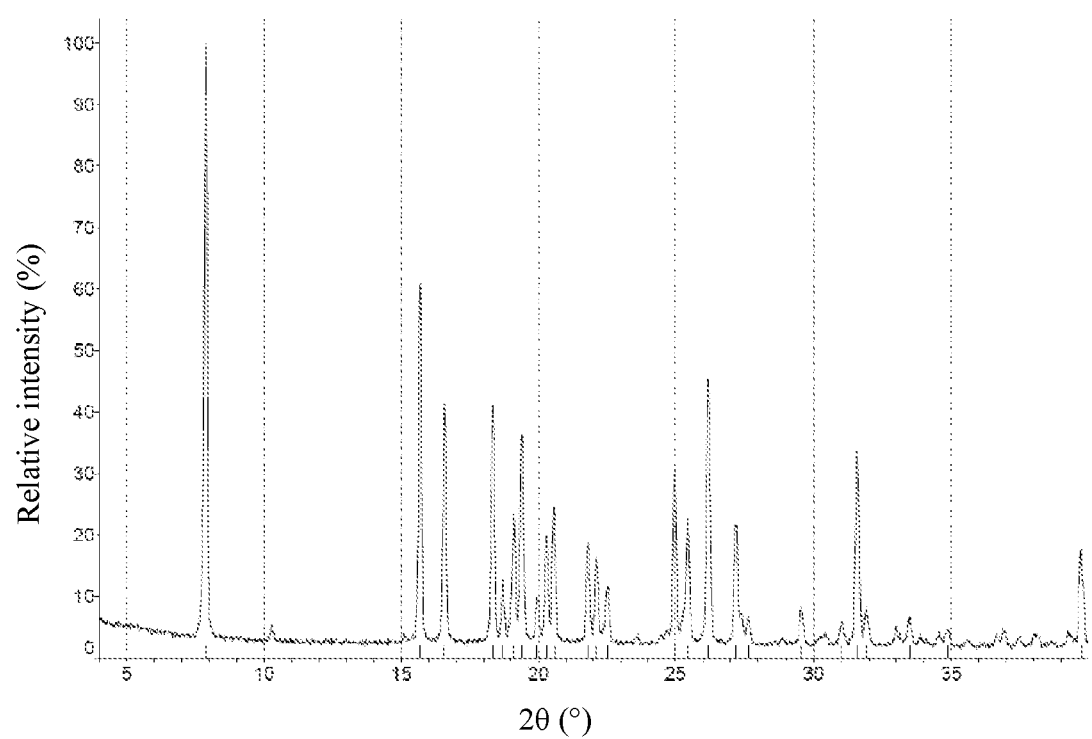
FIG. 1 is the XRPD pattern measured by Cu-Kα radiation of the crystal form A of Compound 1.

In order to better understand the content of the present disclosure, the following examples further illustrate the present disclosure, but the present disclosure is not limited thereto.

Embodiment 1: Synthesis of Compound 1

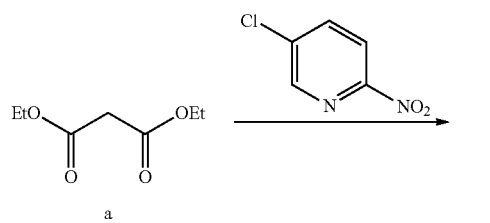

a

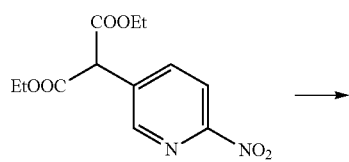

b

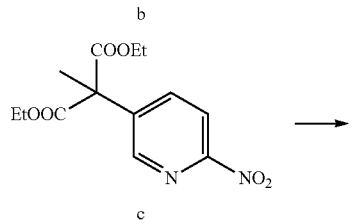

c

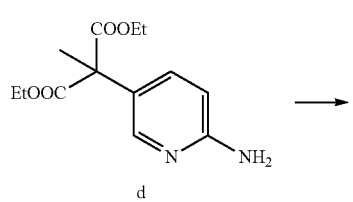

d

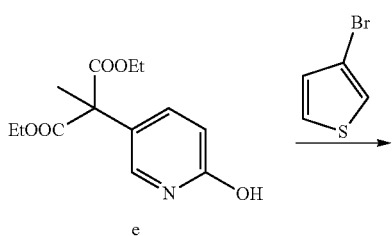

e

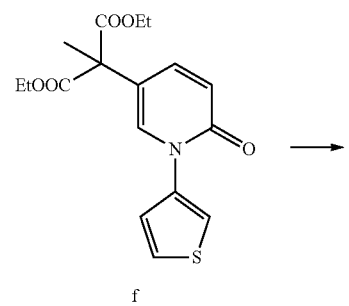

f

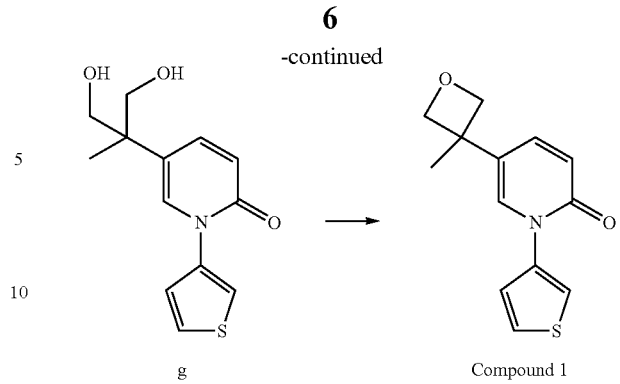

g   Compound 1

Step 1: Synthesis of Compound b

To a suspension of NaH (1.99 g, 49.83 mmol) in anhydrous DMF (75 mL) at 10° C. under $N_2$ atmosphere, was added diethyl malonate (6.57 g, 41.00 mL) dropwise. After completion of the addition, the resulting mixture was stirred for 0.5 hour at room temperature, and then a solution of 5-chloro-2-nitropyridine (5.00 g, 31.54 mmol) in anhydrous DMF (25 mL) was added dropwise. The resulting mixture was slowly warmed to 80° C. and stirred for another 12 hours. After completion of the reaction, the reaction mixture was diluted with water (2300 mL), and then extracted with EtOAc (500 mL*4). The organic phases were combined, washed with saturated brine (100 mL), dried over anhydrous $Na_2SO_4$, filtered to remove the desiccant and the filtrate was concentrated under reduced pressure. The residue was purified by column chromatography (eluent: PE/EtOAc (10/1 to 5/1)) to give Compound b as a tangerine solid (5.40 g, yield 60.66%). $^1$H NMR (400 MHz, $CDCl_3$) δ: 8.63 (d, J=2.0 Hz, 1H), 8.33-8.28 (m, 1H), 8.26 (d, J=2.0 Hz, 1H), 4.81 (s, 1H), 4.33-4.21 (m, 4H), 1.33-1.28 (m, 6H).

Step 2: Synthesis of Compound c

To a solution of Compound b (5.00 g, 17.71 mmol) in anhydrous DMF (50 mL) at room temperature was added potassium carbonate solid (4.90 g, 35.42 mmol), and then methyl iodide (5.03 g, 35.42 mmol) was added dropwise. The resulting mixture was stirred at 25° C. for 1 hour. After completion of the reaction, the reaction mixture was diluted with water (900 mL) and extracted with EtOAc (200 mL*3). The organic phases were combined, washed with saturated brine (50 mL), dried over anhydrous $Na_2SO_4$, filtered to remove the desiccant and the filtrate was concentrated under reduced pressure. The residue was purified by column chromatography (eluent: PE/EtOAc (10/1)) to give Compound c as a yellow solid (5.25 g, yield 100%). $^1$H NMR (400 MHz, $CDCl_3$) δ: 8.67 (d, J=2.0 Hz, 1H), 8.25 (d, J=8.5 Hz, 1H), 8.10 (dd, J=2.5, 8.5 Hz, 1H), 4.27 (dq, J=2.0, 7.1 Hz, 4H), 1.94 (s, 3H), 1.28 (t, J=7.0 Hz, 6H).

Step 3: Synthesis of Compound d

To a solution of Compound c (17.00 g, 60.23 mmol) in EtOAc (150 mL) at room temperature was added 10% wet Pd/C (3.20 g, 3.01 mmol) and the mixture was stirred at 40° C. for 12 hours under the hydrogen atmosphere (50 psi). After completion of the reaction, the reaction mixture was filtered to remove the catalyst and the filter cake was washed with EtOAc (20 mL*3). The filtrate was concentrated under reduced pressure to give Compound d as an orange solid (13.70 g, yield 85.42%), which was used for the next step without further purification. $^1$H NMR (400 MHz, $CDCl_3$) δ: 7.83 (d, J=2.5 Hz, 1H), 7.34 (dd, J=2.5, 8.8 Hz, 1H), 6.45-6.39 (m, 1H), 5.99 (s, 2H), 4.15 (q, J=7.0 Hz, 4H), 1.74-1.66 (m, 3H), 1.17 (t, J=7.0 Hz, 6H).

Step 4: Synthesis of Compound e

At room temperature, Compound d (13.70 g, 51.45 mmol) was dissolved in 70% aq. $H_2SO_4$ (92.00 g, 50 mL), the mixture was cooled to −5° C. and aqueous sodium nitrite (4.30 g, 62.25 mmol) solution (3.5 mL) was added dropwise while maintaining the inner temperature below 0° C. The mixture was stirred at −5° C. for 0.5 hour and then warmed to room temperature, and stirred for another 3 hours. After completion of the reaction, the mixture was diluted with water (800 mL), adjusted pH to 9-10 with saturated aqueous $Na_2CO_3$ solution and then extracted with EtOAc (200 mL*4). The organic phases were combined, washed with saturated brine (50 mL), dried over anhydrous $Na_2SO_4$, filtered to remove the desiccant and rotary evaporated to dryness. The residue was purified by column chromatography (eluent: PE/EtOAc=5/1 to pure EtOAc) to give Compound e as a brown solid (11.00 g, yield 80%). $^1$H NMR (400 MHz, $CDCl_3$) δ: 12.88 (br.s. 1H), 7.60 (dd, J=2.8, 9.8 Hz, 1H), 7.38 (d, J=3.0 Hz, 1H), 6.57 (d, J=9.5 Hz, 1H), 4.23 (q, J=6.9 Hz, 4H), 1.76 (s, 3H), 1.26 (t, J=7.0 Hz, 6H).

Step 5: Synthesis of Compound f

To a solution of Compound e (500.00 mg, 1.87 mmol) and 3-bromo-thiophene (304.88 mg, 1.87 mmol) in anhydrous dioxane (12 mL) was added cuprous iodide (356.14 mg, 1.87 mmol), N,N'-dimethyl-trans-cyclohexanediamine (427.07 mg, 3.74 mmol) and potassium carbonate (516.91 mg, 3.74 mmol) at room temperature under $N_2$ atmosphere, and the resulting mixture was stirred at 100° C. for 12 hours. After completion of the reaction, the reaction mixture was diluted with water (50 mL), and extracted with EtOAc (50 mL). The organic phase was washed with 5% ammonium hydroxide (20 mL*3) until the organic phase turned to luminous yellow and the aqueous phase was not blue. The aqueous phase was extracted with EtOAc (30 mL*2) again. The organic phases were combined and concentrated to dryness under reduced pressure. The residue was purified by column chromatography (eluent: PE/EtOAc from 10/1 to 3/1) to give Compound f as a yellow solid (550.00 mg, yield 84.18%). $^1$H NMR (400 MHz, $CDCl_3$) δ: 7.49 (dd, J=2.6, 9.7 Hz, 1H), 7.44-7.37 (m, 3H), 7.25 (br.d., J=5.3 Hz, 1H), 6.63 (d, J=9.8 Hz, 1H), 4.25 (q, J=7.2 Hz, 4H), 1.77 (s, 3H), 1.28 (t, J=7.2 Hz, 6H).

Step 6: Synthesis of Compound g

To a solution of Compound f (2.95 g, 8.44 mmol) in MeOH (45 mL) was added $NaBH_4$ (1.60 g, 42.20 mmol) in batches at 0° C. under $N_2$ atmosphere, and the resulting mixture was slowly warmed to 25° C. and stirred for 12 hours. After completion of the reaction, the reaction mixture was poured into DCM (450 mL), and stirred for 1 hour at room temperature. The mixture was filtered to remove insolubles and the filtrate was concentrated to dryness under reduced pressure. The residue was purified by column chromatography (eluent: DCM/MeOH from 50/1 to 10/1) to give Compound g as a white powder (950.00 mg, yield 42.42%). $^1$H NMR (400 MHz, DMSO-$d_6$) δ: 7.76-7.72 (m, 1H), 7.67-7.58 (m, 2H), 7.42 (d, J=2.5 Hz, 1H), 7.31-7.27 (m, 1H), 6.45 (d, J=9.5 Hz, 1H), 4.65 (br.s., 2H), 3.56-3.49 (m, 2H), 3.48-3.42 (m, 2H), 1.11 (s, 3H).

Step 7: Synthesis of Compound 1

To a solution of Compound g (900.00 mg, 3.39 mmol), triphenylphosphine (1.78 g, 6.78 mmol) and ziram (1.60 g, 5.22 mmol) in anhydrous THF (25 mL) was added DEAD (1.18 g, 6.78 mmol) dropwise at room temperature under $N_2$, and the resulting mixture was stirred at 30° C. for 20 hours. After completion of the reaction, MeOH (50 mL) was added to the mixture, followed by filtration to remove the insolubles, and the solid was washed with MeOH (10 mL*2). The filtrates were combined and concentrated to dryness under reduced pressure. The residue was purified by column chromatography (eluent: PE/EtOAc from 10:1 to pure EtOAc) to give a yellow crude product containing a small amount of triphenylphosphine oxide. The crude product was slurried with a mixed solvent of PE and EtOAc (1:1, 10 mL) for 1 hour and then filtered to collect the solid. The filter cake was washed with PE (5 mL*2) and the obtained solid was dried under vacuum to give Compound 1. $^1$H NMR (400 MHz, $CDCl_3$) δ: 7.60 (dd, J=2.5, 9.5 Hz, 1H), 7.46-7.39 (m, 2H), 7.27-7.22 (m, 2H), 6.78 (d, J=9.5 Hz, 1H), 4.80 (d, J=6.0 Hz, 2H), 4.63 (d, J=5.8 Hz, 2H), 1.72-1.65 (m, 1H), 1.69 (s, 2H).

Embodiment 2: Synthesis of Crystal Form A

Ethyl acetate (800 mL) was added to Compound 1 (163 g), and the mixture was slightly heated to completely dissolve the solid. The resulting mixture was filtered by suction filtration with a #6 sand core funnel to remove impurities and insolubles, and the filtrate was rotary-evaporated to dryness. To the residue was added n-heptane/ethyl acetate (1:1, 800 mL), and the resulting mixture was stirred and slurried at room temperature for 12 hours, followed by filtration to collect the insolubles. The obtained white solid was detected by HPLC (mobile phase A: 0.05% aqueous trifluoroacetic acid solution; mobile phase B: acetonitrile; column: Ultimate C18 3.0 mm×50 mm, 3.0 µm; peak time: 8 min) to confirm the purity being higher than 98%. If the purity was unqualified, the slurrying operation was repeated (generally no more than 2 times) until the purity reached the requirement. 122 g of crystal form A of Compound 1 was obtained as a white solid powder. $^1$H NMR (400 MHz, DMSO-$d_6$) δ: 1.07 (s, 3H), 3.37-3.44 (m, 2H), 3.44-3.52 (m, 2H), 6.40 (d, J=9.48 Hz, 1H), 7.25 (dd, J=5.18, 1.43 Hz, 1H), 7.38 (d, J=2.65 Hz, 1H), 7.54-7.63 (m, 2H), 7.67-7.71 (m, 1H).

Experimental Embodiment 1: Solid-State Stability Test of the Crystal Form A Under High Temperature and High Humidity Conditions 16 samples of 10 mg of crystal form A were weighed in parallel and spread evenly on the bottom of glass bottles, and 8 samples of 20 mg of crystal form A were spread out into a thin layer. All sample bottles were sealed with aluminum foil, and some small holes were punched on the aluminum foil to allow the samples to fully contact with the ambient air. The samples were placed at 40° C./75% RH and 60° C./75% RH for 1 month, 2 months and 3 months, respectively.

Analytical method: Agilent 1260 HPLC with DAD detector or Waters 2695 HPLC with PDA detector was used: column: Waters Atlantis dC18 (4.6 mm×150 mm, 3.0 µm); column temperature: 40° C.; flow rate: 1.0 mL/min; detection wavelength: 230 nm; injection volume: 10 µL; sample concentration: 0.5 mg/mL; diluent: acetonitrile:water=1:1 (v/v); the following mobile phase gradients were used for analysis:

| Gradient: Time (min) | Mobile phase A: 0.04% TFA in water (%) | Mobile phase B: ACN (%) |
|---|---|---|
| 0.00 | 95 | 5 |
| 50.00 | 50 | 50 |
| 55.00 | 30 | 70 |
| 55.01 | 95 | 5 |
| 60.00 | 95 | 5 |

Table 2: Solid-State Stability Test of Crystal Form A

TABLE 2

Solid-state stability test of crystal form A

| Storage conditions | | Appearance | Crystal form | Purity (%) | Total impurities (%) |
|---|---|---|---|---|---|
| 40° C./ 75% RH | 1 M | White powder | Form A | 99.949 | 0.051 |
| | 2 M | White powder | Form A | 99.948 | 0.052 |
| | 3 M | White powder | Form A | 99.947 | 0.053 |
| 60° C./ 75% RH | 1 M | White powder | Form A | 99.949 | 0.051 |
| | 2 M | White powder | Form A | 99.948 | 0.052 |
| | 3 M | White powder | Form A | 99.950 | 0.050 |

Experimental conclusion: The crystal form A is stable within three months under each condition, showing it has good druggability.

Experimental Embodiment 2: Solid-State Physical Stability Test of the Crystal Form A Under Conditions of Different Temperature, Humidity and Light Irradiation 4 samples of 100 mg of crystal form A solid were weighed in parallel and spread evenly on the bottom of the glass bottles into a thin layer. The bottles were sealed with aluminum foil, and some small holes were punched on the aluminum foil to allow the sample to be fully in contact with the ambient air. The 4 samples prepared were placed under the conditions of 25° C./92.5% RH, 60° C., 40° C./75% RH and light irradiation, and the physical stability of the samples on the 10th day was examined. In the meantime, about 100 mg of crystal form A solid was weighed separately, placed on the bottom of a glass sample bottle, sealed with a screw cap and stored at −20° C., this sample was used as the control sample. On the 10th day, all samples were taken out, and returned to room temperature. The appearance change of the samples was observed, and XRPD was used to detect the crystal form of the samples. By comparing the accelerated samples with the control sample, the solid-state physical stability of crystal form A of Compound 1 was determined. The following Table 3 shows the experimental results of the solid-state physical stability of crystal form A.

TABLE 3

Solid-state physical stability test of the crystal form A under conditions of different temperature, humidity and light irradiation

| Item | Time point | Day 0 (−20° C. sealed storage) (Control sample) | 25° C./ 92.5% RH (open) | 60° C. (open) | 40° C./ 75% RH (open) | Light irradiation |
|---|---|---|---|---|---|---|
| Crystal form | 10 d | Form A | Form A | Form A | Form A | Form A |
| Appearance | 10 d | White powder | White powder | White powder | White powder | White powder |

Experimental conclusion: The crystal form A is stable within 10 days under each condition, showing it has good druggability.

Experimental Embodiment 3: Study on Polymorphism of Compound 1

Approximate 50 mg of the sample were weighed and added to separate 4.0 mL glass vials, respectively, followed by addition of an appropriate amount of the solvents or solvent mixture (see the table below) to give a suspension. After shaking at 40° C. for 2 days, all the samples were taken out and centrifuged in a centrifuge at 8000 r/min for 5 minutes. The supernatant was discarded, and the remaining solid was dried in a 35° C. vacuum drying box for two days. The dried samples were taken out for XRPD detection.

TABLE 4

Results of the study on polymorphism of Compound 1

| No. | Solvent | Crystal form |
|---|---|---|
| 1 | Ethanol | Form A |
| 2 | Acetonitrile | Form A |
| 3 | Acetone | Form A |
| 4 | Ethyl acetate | Form A |
| 5 | Acetone:Water (1:2) | Form A |
| 6 | Water | Form A |

Experimental conclusion: It is indicated from the above table that the crystal form A of Compound 1 is stable under the conditions of the above solvents.

Experimental Embodiment 4: Solubility of the Crystal Form A in Different Solvents In this study, the method of manual stepwise dilution along with the observation of the dissolution under ambient temperature condition was used for determination. About 2 mg of crystal form A of Compound 1 was added to separate HPLC vials, followed by multiple addition of organic solvents or the mixed solvents (Table 5) in a small amount, and the dissolution of the compound was monitored. The solubility test results of the compound are shown in Table 5.

TABLE 5

Approximate solubility of the crystal form A in different solvents

| No. | Solvent | Solubility (mg/mL) |
|---|---|---|
| 1 | Methanol | >104 |
| 2 | Ethanol | 51-102 |
| 3 | Isopropanol | 34-52 |
| 4 | n-butanol | 50-100 |

TABLE 5-continued

Approximate solubility of the crystal form A in different solvents

| No. | Solvent | Solubility (mg/mL) |
|---|---|---|
| 5 | Acetonitrile | >100 |
| 6 | Acetone | 52-103 |
| 7 | Methyl ethyl ketone | 52-104 |
| 8 | Methyl isobutyl ketone | 34-51 |

TABLE 5-continued

Approximate solubility of the crystal form A in different solvents

| No. | Solvent | Solubility (mg/mL) |
|---|---|---|
| 9 | Ethyl acetate | 34-51 |
| 10 | Isopropyl acetate | 20-34 |
| 11 | Methyl tert-butyl ether | <2 |
| 12 | Tetrahydrofuran | 51-102 |
| 13 | 2-Methyltetrahydrofuran | 34-51 |
| 14 | Toluene | 35-52 |
| 15 | Heptane | <2 |
| 16 | Cyclohexane | <2 |
| 17 | 1,4-dioxane | >102 |
| 18 | Water | 10-21 |
| 19 | Methanol-water (1:1) | >102 |
| 20 | Methanol-water (3:1) | >104 |
| 21 | Ethanol-water (1:1) | >100 |
| 22 | Ethanol-water (3:1) | >104 |
| 23 | Acetonitrile-water (1:1) | >100 |
| 24 | Acetone-water (1:2) | 52-103 |
| 25 | Isopropanol-water (1:1) | >102 |

Experimental Embodiment 5: Ex-Vivo Evaluation of the Effect of the Compound on Endotoxin LPS-Induced TNF-α in Rat Blood Experimental objective: testing the effect of Compound 1 on bacterial lipopolysaccharide (LPS)-induced TNF-α in rat blood to evaluate the anti-inflammatory effect ex-vivo Experimental Materials:

Sprague Dawley rats (male, 280-310 g, Shanghai Slac Laboratory Animal CO. LTD)

Rat TNF-alpha Quantikine ELISA Kit (R&D, #SRTA00)

Experimental Procedure:

A solution of the compound was prepared (5 mM or 1 mM), and 40 µL of the prepared solution was added into a 48-well cell culture plate, respectively (the final concentration of the compounds was 0.5 or 0.1 mM). The rats were anaesthetized with isoflurane and the blood was collected from the abdominal aorta (Heparin anticoagulant). The blood was added into the 48-well cell culture plate (320 µL per well) containing the compounds to be tested. Afterwards, the 48-well cell culture plate was incubated at 37° C. for 30 minutes. Then the plate was taken out, and 40 µL of LPS (the final concentration was 100 µg/mL) was added and mixed evenly. The resulting mixture was incubated at 37° C. After 5 hours, the 48-well plate was taken out and the blood was transferred into 1.5 mL centrifuge tubes and centrifuged in a centrifuge (4,500 rpm, 4° C., 5 min). The supernatant was isolated to obtain the plasma, which was aliquoted (20 µL per well) into a 96-well sample plate, and then sharp-frozen and preserved in a refrigerator (−80° C.). On the second day, the TNF-α level in the plasma samples was determined by using R&D ELISA kits according to the kit specification. The data was analyzed by EXCEL and Prism.

Summary of Experimental Results:

TABLE 6

| Embodiment | Ex-vivo inhibition of TNF-α |
|---|---|
| Pirfenidone (PFD) | 53.51% ± 5.73 |
| Compound 1 (crystal form A) | 80.78% ± 5.67 |

Note:
the concentration of PFD was 0.5 mM, while that of Compound 1 was 0.1 mM.

Conclusion: in the ex-vivo experiment of inhibitory effect on TNF-α, the crystal form A of Compound 1 with a final concentration of 0.1 mM exhibits a significant inhibitory effect on TNF-α level induced by LPS, and the inhibition is significantly higher than original drug Pirfenidone.

What is claimed is:

1. A crystal form A of Compound 1, wherein the crystal form A has an X-ray powder diffraction pattern comprising characteristic peaks at diffraction angle 2θ of 7.87±0.2°, 15.69±0.2° and 16.58±0.2°;

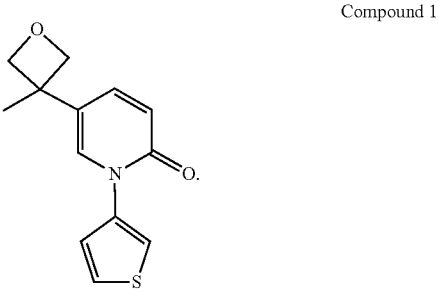 [SMILES: CC1(c2ccc(=O)n(-c3ccsc3)c2)COC1]

Compound 1

2. The crystal form A of Compound 1 as defined in claim 1, wherein the X-ray powder diffraction pattern comprises characteristic peaks at diffraction angle 2θ of 7.87±0.2°, 15.69±0.2°, 16.58±0.2°, 18.34±0.2°, 19.39±0.2°, 24.97±0.2°, 27.19±0.2° and 31.57±0.2°.

3. The crystal form A of Compound 1 as defined in claim 2, wherein the X-ray powder diffraction pattern comprises characteristic peaks at diffraction angle 2θ as shown in FIG. 1.

4. The crystal form A of Compound 1 as defined in claim 1, wherein the crystal form A has a differential scanning calorimetry curve having an endothermic peak with an onset of 106.63° C.±4° C.

Figure 2:
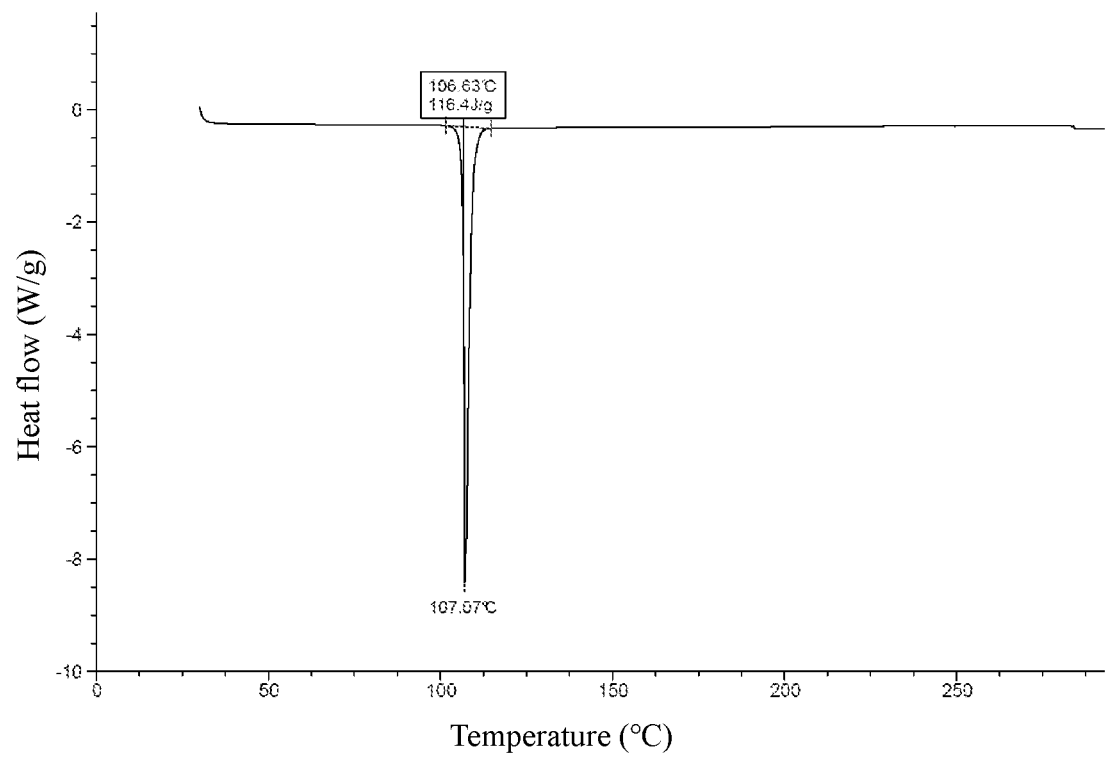
FIG. 2 is the DSC pattern of the crystal form A of Compound 1.

5. The crystal form A of Compound 1 as defined in claim 4, wherein the crystal form A has a differential scanning calorimetry pattern as shown in FIG. 2.

6. The crystal form A of Compound 1 as defined in claim 1, wherein the crystal form A has a thermogravimetric analysis curve having a weight loss of 0.3391% occurred at 110.00° C.±3° C.

Figure 3:
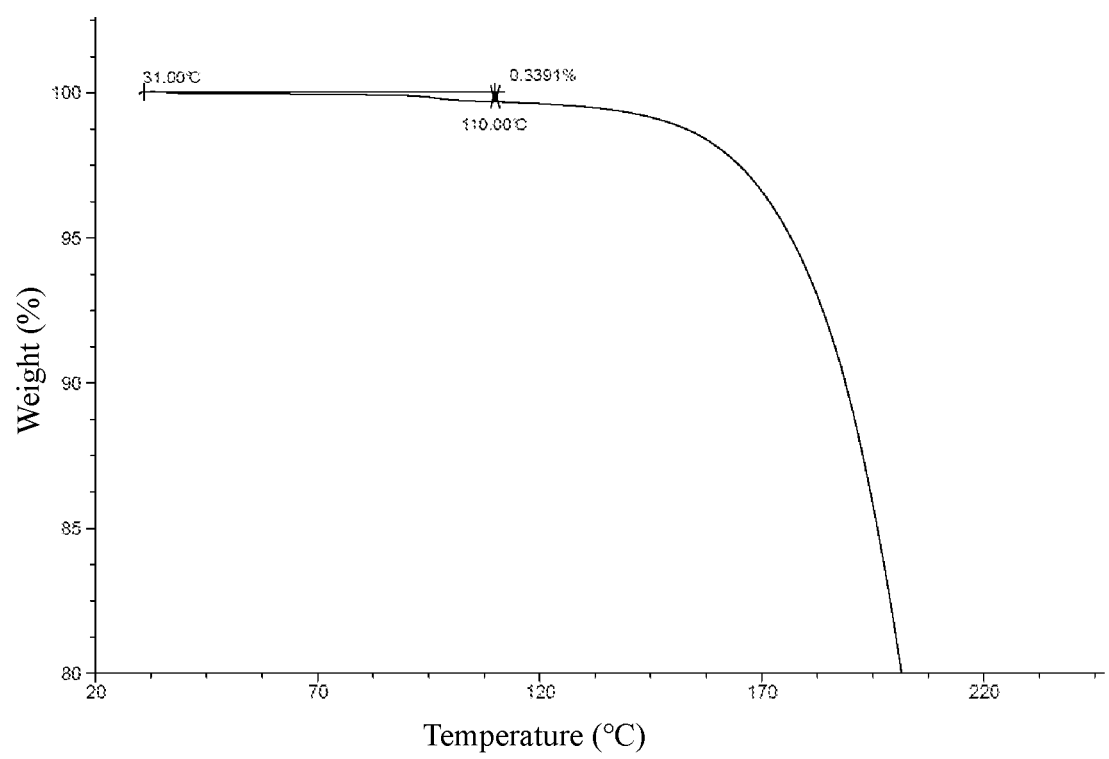
FIG. 3 is the TGA pattern of the crystal form A of Compound 1.

7. The crystal form A of Compound 1 as defined in claim 6, wherein the crystal form A has a thermogravimetric analysis pattern as shown in FIG. 3.

8. A pharmaceutical composition comprising the crystal form A of Compound 1 as defined in claim 1 and at least one pharmaceutically acceptable excipient.

9. A method for treating idiopathic pulmonary fibrosis in a subject in need thereof, comprising administering to the subject a therapeutically effective amount of the pharmaceutical composition as defined in claim 8.

10. A method for treating idiopathic pulmonary fibrosis in a subject in need thereof, comprising administering to the subject a therapeutically effective amount of the crystal form A of Compound 1 as defined in claim 1.

11. A method for preparing a crystal form A of Compound 1, comprising adding the Compound 1 existing in any form to an organic mixed solvent of an ester solvent and an alkane solvent and slurrying to obtain the crystal form A of Compound 1;

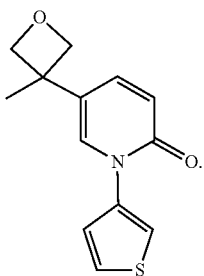

Compound 1

12. The method as defined in claim 11, wherein the ester solvent is ethyl acetate.

13. The method as defined in claim 11, wherein the alkane solvent is one or more selected from the group consisting of petroleum ether, n-heptane and cyclohexane.

14. The method as defined in claim 11, wherein the organic mixed solvent is a mixed solvent of ethyl acetate and n-heptane.

15. The method as defined in claim 14, wherein the volume ratio of the ethyl acetate to n-heptane is 1:0.5-1.5.

16. The method as defined in claim 15, wherein the volume ratio of the ethyl acetate to n-heptane is 1:1.

17. The method as defined in claim 11, wherein the slurrying is performed at a temperature of 20° C. to 30° C.

18. The method as defined in claim 11, wherein the duration of the slurrying is 12 hours to 36 hours.

19. The method as defined in claim 11, wherein the weight ratio of the Compound 1 to the organic mixed solvent is 1:5-6.

* * * * *